United States Patent
Traidia et al.

(10) Patent No.: US 10,473,569 B2
(45) Date of Patent: Nov. 12, 2019

(54) METHOD AND DEVICE FOR TESTING A MATERIAL SAMPLE IN A STANDARD TEST FOR IN-PLANE FRACTURE TOUGHNESS EVALUATION

(71) Applicant: Saudi Arabian Oil Company, Dhahran (SA)

(72) Inventors: Abderrazak Traidia, Abqaiq (SA); Elias Chatzidouros, Attiki (GR); Mustapha Jouiad, Abu Dhabi (AE)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 15/858,273

(22) Filed: Dec. 29, 2017

(65) Prior Publication Data

US 2018/0364138 A1    Dec. 20, 2018

Related U.S. Application Data

(60) Provisional application No. 62/520,489, filed on Jun. 15, 2017.

(51) Int. Cl.
*G01N 3/02* (2006.01)
*G01N 3/20* (2006.01)
(Continued)

(52) U.S. Cl.
CPC .............. *G01N 3/02* (2013.01); *G01N 3/04* (2013.01); *G01N 3/20* (2013.01); *G01N 1/04* (2013.01);
(Continued)

(58) Field of Classification Search
CPC .... G01N 3/02; G01N 3/20; G01N 2203/0064; G01N 2203/0298; G01N 2203/027
(Continued)

(56) References Cited

U.S. PATENT DOCUMENTS 4,916,954 A * 4/1990 Buzzard .................. G01N 3/08
 73/799
5,641,912 A * 6/1997 Manahan, Sr. .......... G01N 3/18
 374/50
(Continued)

FOREIGN PATENT DOCUMENTS

DE    2557720 A1 *  7/1977   ............... G01N 3/30
DE    2557720 A1     7/1977

OTHER PUBLICATIONS

Koch, Gerhardus. "Tests for Stress-Corrosion". Advanced Materials & Process. Aug. 2001. <https://www.asminternational.org/documents/10192/1755223/amp15908p036.pdf/026e7c61-4606-424e-9ade-3455865aba71> (Year: 2001).*

(Continued)

*Primary Examiner* — Jonathan M Dunlap
(74) *Attorney, Agent, or Firm* — Leason Ellis LLP

(57) ABSTRACT

A method of testing a material sample of a type used in a wall of a structure in a standard test for in-plane fracture toughness evaluation. The method comprises obtaining a sample having a lateral length no larger than a thickness of the wall of the structure, shaping the sample to have (a) a bottom surface, (b) a profiled top surface having a central notch, (c) a first coupling feature on a first side of the central notch, and (d) a second coupling feature on a second side of the central notch, assembling a test specimen which increases the width of the sample beyond the lateral width by coupling a first lateral extension to the first coupling feature and a second lateral extension to the second coupling feature, and applying a standard fracture toughness test to the so-assembled test specimen and sample to evaluate the fracture toughness of the sample.

6 Claims, 14 Drawing Sheets

(51) Int. Cl.
 *G01N 3/04* (2006.01)
 *G01N 1/04* (2006.01)
 *G01N 1/28* (2006.01)
(52) U.S. Cl.
 CPC ............... *G01N 2001/2886* (2013.01); *G01N 2203/0064* (2013.01); *G01N 2203/0066* (2013.01); *G01N 2203/027* (2013.01); *G01N 2203/0298* (2013.01)
(58) Field of Classification Search
 USPC .......................................... 73/849, 799, 856
 See application file for complete search history.

(56) References Cited

U.S. PATENT DOCUMENTS

| | | | |
|---|---|---|---|
| 6,543,273 B1 | 4/2003 | Wells et al. | |
| 2011/0094307 A1* | 4/2011 | Seok | G01N 3/04 |
| | | | 73/851 |
| 2018/0238783 A1* | 8/2018 | Willan | G01N 3/02 |

OTHER PUBLICATIONS

Chatzidouros E C et al: "Hydrogen effect on fracture toughness of pipeline steel welds, with in situ hydrogen charging", International Journal of Hydrogen Energy, Elsevier Science Publishers B.V., Barking, GB, vol. 36, No. 19, Jun. 29, 2011, pp. 12626-12643.

* cited by examiner

METHOD AND DEVICE FOR TESTING A MATERIAL SAMPLE IN A STANDARD TEST FOR IN-PLANE FRACTURE TOUGHNESS EVALUATION

CROSS-REFERENCE TO RELATED APPLICATIONS

The application claims priority to U.S. Provisional Application Ser. No. 62/520,489, filed on Jun. 15, 2017, having the same title, which is hereby incorporated by references as if set forth in its entirety herein.

FIELD OF THE INVENTION

The present invention relates to the testing of materials for structural fitness, and, more particularly, relates to a method and device for testing a material sample of relatively small thickness in a standard test for in-plane fracture toughness evaluation.

BACKGROUND OF THE INVENTION

Hydrogen-induced cracking (HIC) is encountered by oil and gas pipelines and related installations with sour environments having high hydrogen sulfide ($H_2S$) concentrations. These defects are attributable to atomic hydrogen produced by sour corrosion that enters the bulk of the steel. The atomic hydrogen reacts and recombines to form high pressure molecular hydrogen cavities at the interface of nonmetallic spaces residing in the microstructure. HIC tends to propagate in a plane parallel to the pipe wall as shown in FIG. 1, which shows examples of cracks induced by HIC. Fracture toughness (FT) tests are standardized mechanical tests design to measure the resistance of a material to crack growth. In FT tests, a pre-cracked test specimen is loaded under a controlled displacement rate while measuring the resulting force. A force-displacement curve is used to calculate FT parameters such as a plain strain stress intensity factor (K) and a J-integral (J).

When carrying out fracture toughness (FT) tests to characterize the ability of the material to resist crack propagation, the dimensions and orientation of the FT specimen are critical. The dimensions of a rectangular forged/rolled plate sample are defined as the longitudinal (L) which is parallel to the plate rolling/forging direction, the transverse dimension (T) and the short transverse or thickness dimension (S). A schematic model of a sample illustrating these planes is shown in FIG. 2. The first letter denotes the direction normal to the crack plane (which coincides with the direction of the principal tensile stress for Model I fracture), while the second letter denotes the direction of crack extension.

The directions of interest for HIC crack propagation and more generally, stepwise cracking, are the S-T or S-L directions shown in FIG. 2, which are the directions in which parallel in-plane cracks occur. It has proven to be difficult to measure fracture toughness (FT) properties for thin or relatively thin pipelines (10-30 mm wall thickness) in these directions. This is particularly problematic, as often the FT values in the SL and ST direction are not equal to the FT values in the other directions (e.g. TL, LT), so that measurements taken in the other directions cannot be used as a reliable estimate for the FT values in the SL and ST directions.

The ASTM (American Society for Testing and Materials) 1820 fracture toughness test standard requires use of specific specimens, of either a single edge bending (SEB) or a compact tension (CT) type. However, such specimens are not suited for FT measurements in S-T and S-L directions because there is not enough material in the thickness direction to extract a full SEB or CT specimens. For example, to machine a typical SEB specimen of 10 millimeter thickness requires a minimum plate thickness of about 90 millimeters, which is well above common pipe thicknesses of pipe equipment used in the oil and gas industries.

While in-plane FT data is not required to design against fracture of metallic structures, it becomes of high interest when the equipment of interest may develop in-plane cracks such as HIC. Such data can help at the material selection stage to discriminate between different types of steel, the quality of metal provided by different manufacturers, and also can enable prediction of crack growth rate and their impact on the residual integrity of the equipment during their service life.

What is therefore need is a methodology to enable FT tests for in-plane fractures that can produce valid measurements (i.e., compliant with the Standard) of the in-plane fracture toughness of metallic plates. It is with respect to these and other considerations that the disclosure made herein is presented.

SUMMARY OF THE INVENTION

Embodiments of the present invention provide methods of testing a material in a standard test for in-plane fracture toughness evaluation, in which the material sample is of a type used in a wall of a structure. In certain embodiments, the method comprises obtaining a sample of the wall of the structure, shaping the sample into a notched component, the notched component including a flat bottom surface having a thickness dimension equal to a thickness of the wall of the structure, and a profiled top surface, the profiled top surface having a central notch oriented perpendicular to a plane of the bottom surface, a first socket on a first side of the central notch, and a second socket on a second side of the central notch, assembling a test specimen which increases an effective thickness of the sample beyond the thickness of the bottom surface of the notched component by coupling a first lateral extension to the first socket and a second lateral extension to the second socket of the notched component, and applying a standard fracture toughness test to the so-assembled test specimen in order to evaluate the fracture toughness of the material in an in-plane direction. The structure to be tested is preferably a material with a thickness between about 5 mm and about 70 mm, such as a steel pipe prevalently used in the oil and gas industry.

In some implementations, methods of the present invention further comprise machining the notched component such that the central notch is oriented to open in a T-L direction in a standard fracture toughness test. In other implementations, the methods further comprise machining the notched component is shaped such that the central notch is oriented to open in a S-L direction in a standard fracture toughness test.

To meet the requirements of standard fracture tests, it is preferable to form the first and second lateral extensions such that a sum of the lengths of the first and second lateral extensions and the thickness of the notched component is as great, or greater than, 4.5 times the width of the notched component as measured from the bottom surface to a tip of the profiled surface.

In some embodiments, the first and second sockets can be symmetrical about the central notch, while in other embodiments the first and second sockets can be asymmetrical about the central notch. The test specimen can be placed in a standard fracture toughness test apparatus such that force is applied the bottom surface of the notched component. The central notch of the notched component can be shaped to include a first section having a first width and a second section positioned beneath the first section having a second width that is smaller than the first width. The first and second sockets of the notched component can form elbow-shaped notches.

In some embodiments, the method further includes performing a finite element simulation of fracture toughness using a programmed computer and data from the standard fracture toughness test to determine optimal geometric parameters for the notched component.

To investigate the effects of a harsh hydrogen environment on test specimens, in some embodiments the method further comprises charging the notched component with hydrogen prior to applying the standard fracture test. In such embodiments, the notched component can be charged with hydrogen over a duration until the hydrogen concentration reaches a desired level. The current density required to charge the notched component to a target steady-state hydrogen concentration can also be determined, as well as the difference in fracture properties between S-L and T-L directions at a plurality of hydrogen concentration levels.

Embodiments of the present invention also provide an apparatus for testing a material used in a wall of a structure for fracture toughness. Embodiments of the apparatus comprise a notched component made from a sample of the material of the structure shaped to have (a) a bottom surface having a width equal to a thickness of the wall of the structure, (b) a profiled top surface, the profiled top surface having a central notch, (c) a first socket on a first side of the central notch, and (d) a second socket feature on a second side of the central notch, a first lateral extension coupled to the first socket of the notched component, and a second lateral extension coupled to the second socket of the notched component. The first and second lateral extensions extend an effective width of the notched component to provide an assembled test specimen of sufficient length to be used in a standard fracture toughness test. The structure is preferably a material having a relatively small thickness between about 5 mm and about 70 mm, such as a wall of a pipe made of steel, such as X65.

In some embodiments, the central notch of the notched component is oriented to open in a T-L direction in a standard fracture toughness test. In other embodiments, the central notch of the notched component is oriented to open in a S-L direction in a standard fracture toughness test.

The first and second lateral extensions can be formed such that a sum of the lengths of the first and second lateral extensions and the thickness of the notched component is as great or greater than 4.5 times the width of the notched component as measured from the bottom surface to a tip of the profiled surface.

In some implementations, the central component is charged with hydrogen.

These and other aspects, features, and advantages can be appreciated from the following description of certain embodiments of the invention and the accompanying drawing figures and claims. The drawings are illustrative and exemplary, and do not necessarily accurately indicate the scale, either in an absolute sense, or a relative sense, of the elements depicted.

BRIEF DESCRIPTION OF THE DRAWINGS

FIGS. 8A to 8D are schematic representations of fracture toughness tests performed on integral specimens of two different thickness (FIGS. 8A, 8B), and assembled test specimens of two different thicknesses (FIGS. 8C, 8D).

DETAILED DESCRIPTION OF CERTAIN EMBODIMENTS OF THE INVENTION

Embodiments of the present invention provide a method and device for enabling FT tests of samples in the S-L and S-T directions, which provides HIC information. An assembled test specimen is provided which has dimensions that are compatible and compliant with standard fracture toughness test requirements. The specimen comprises a sample taken from the material of interest (e.g., a mother steel plate) that is machined to include a notch that matches a crack orientation in the S-L or S-T directions.

Figure 1:
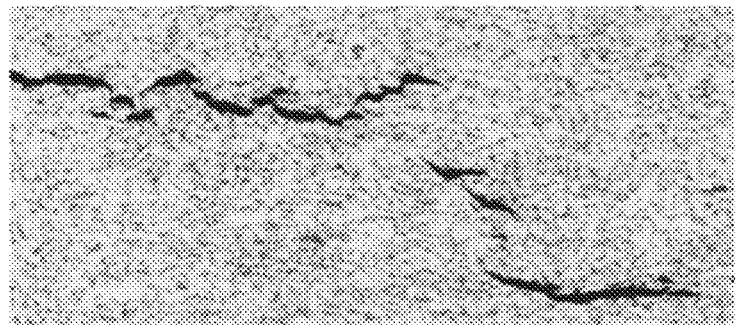
FIG. 1 depicts an example of hydrogen-induced cracking (HIC).
Figure 2:
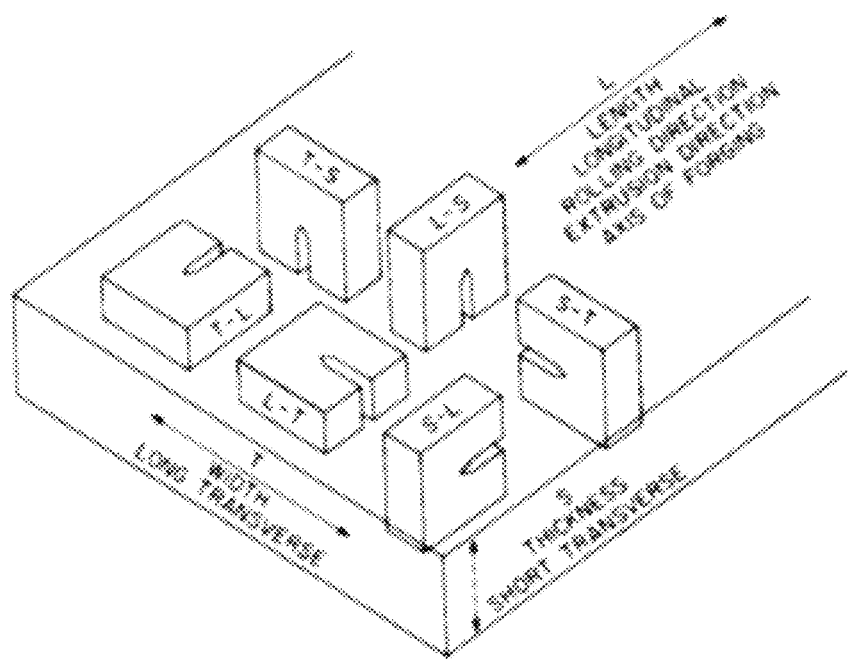
FIG. 2 is a schematic perspective view showing ASTM terminology for planar directions related to fracture toughness testing.
Figure 3:
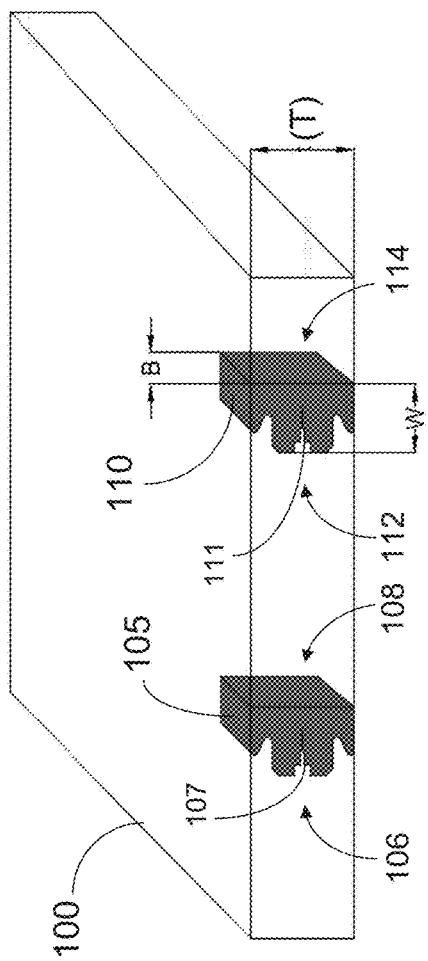
FIG. 3 is a schematic perspective view of notched components according to an embodiment of the present invention.

FIG. 3 is a schematic perspective view that depicts a plate 100 having a thickness (T) made of material (e.g., a type of steel) to be tested for fracture toughness. The plate 100 can be a sample of a pipe or is otherwise has a thickness representative of the thickness of pipes used in the industry, of about 10 mm to about 30 mm. Within the plate 100, two example notched components 105, 110 that are adapted for fracture toughness tests according to the present invention are shown in outline. The notched components 105, 110 can be machined out of the plate by a subtractive technique such as milling, laser cutting, etc. As indicated, the respective front faces 106, 112 of components 105, 110 are notched, while the respective rear faces 108, 114 of the components are flat. The length of the front and rear faces of the notched components precisely matches the thickness (T) of the plate 100. The front face 106 of notched component 105 includes a central notch 107 that is oriented parallel to the plane of the plate 100, i.e., horizontally. Similarly, the front face 112 of notched component 110 includes a central notch 111 that is oriented parallel to the plane of the plate 100. Central notches 107, 111 represent a hydrogen-induced crack oriented in the plane of the plate in the S-L or S-T direction. In the embodiments depicted in FIG. 3, the front faces 106, 112 of the specimens have a "W" shaped profile to enable easy mechanical assembly with additional components.

Figure 4A:
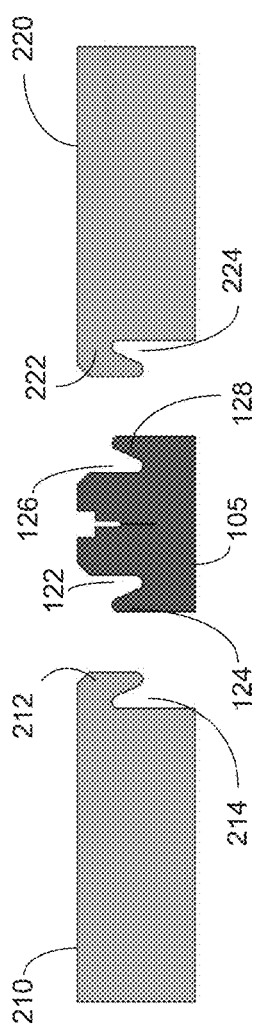
FIG. 4A is a schematic front plan view of an embodiment of a test specimen according to the present invention pre-assembly.

FIG. 4A is a front view of an embodiment of a pre-assembled test specimen 200 according to an embodiment of the present invention. The test specimen 200 includes three components: a notched component e.g., 105, as shown in FIG. 3, a first lateral extension 210 adapted to securely couple to a first lateral side of the notched component 105, and a second lateral extension 220 adapted to securely coupled to a second lateral side of the notched component 105. The first and second lateral extensions 210, 220 are made either of the same material as the notched component (e.g., machined from the same original plate), or of a high strength material. As assembled, the notched component and the first and second lateral extensions increase the effective length of the test specimen.

In the embodiment depicted, the notched component 105, in addition to a central notch 107, a first half of the "W" shaped profile is formed, on a first side of the component (left side in FIG. 4A), of a socket 122 (female connector) positioned adjacent to the central notch 107, and an upward curving, hook-shaped tab 124 (male connector) positioned adjacent to the socket 122 opposite the central notch. A second half of the "W" shaped profile is formed, on the second side of the component (right side in FIG. 4A), of a second socket 126 positioned adjacent to the central notch 107, and a second upward curving, hook-shaped tab 128 positioned adjacent to the second socket 126 opposite the central notch.

The end of the first lateral extension 210 shown adjacent to the notched component 105 includes a downward curving, hook-shaped tab 212 adapted to precisely and snugly fit into the first socket 122 of the notched component. Adjacent to tab 212 on lateral extension 210 is a socket 214 that is adapted to snugly receive the first tab 124 of the notched component. Similarly, the end of the second lateral extension 220 shown adjacent to the notched component 105 includes a downward curving, hook-shaped tab 222 adapted to precisely and snugly fit into the second socket 126 of the notched component. Adjacent to tab 222 on second lateral extension 220 is a socket 224 that is adapted to snugly receive the second tab 128 of the notched component.

Figure 4B:
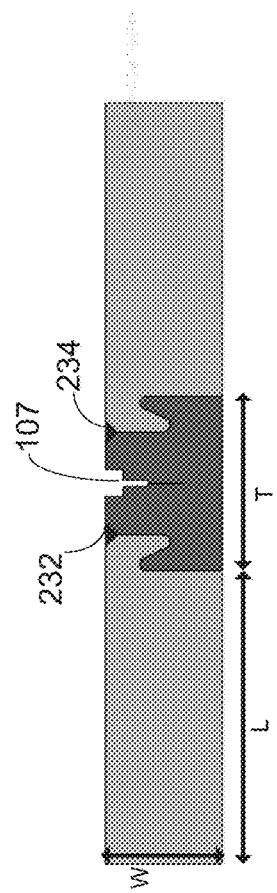
FIG. 4B is a schematic front plan view of an embodiment of an assembled test specimen according to the present invention.

FIG. 4B is a front view of the test specimen as assembled by inserting the tabs 212, 222 of the first and second lateral extensions 210, 220 into the respective sockets 122, 126 of the notched component 105, as simultaneously, the tabs 124, 128 of the notched component are inserted into the respective sockets 214, 224 of the first and second lateral extensions. Weld joints 232, 234 can be formed where the top surfaces of the first and second lateral extensions 210, 220 contact the notched component as shown in FIG. 4B. The weld joints 232, 234 firmly secure the lateral extensions 210, 220 to the notched component 105. In some implementations, weld joints 232, 234 can be produced by micro-laser welding which introduces very little heat into the specimen and does not affect (thermally) the area around the crack zone (central notch 111). To ensure that the welding does not thermally affect the region around the central notch 111, a commercial welding simulation tool (such as SYSWELD produced by the EGI Group of Paris, France) is used to simulate the welding process in order to obtain an estimate of actual welding parameters (precise placement, temperature, time) to use during micro-laser welding.

The length of the lateral extensions can be configured so that the assembled test specimen complies with the following equation set forth in standard test requirements:

$$2L+T \geq 4.5W \quad (1)$$

in which L represents the lengths of the lateral extensions (in embodiments in which the extensions are the same length), W measures the width of the notched component, measured as the distance from the top edge of the front face 106 to the back edge of the rear face 108 of the notched component, and T measures the thickness of the sample, which, as noted above, corresponds to the thickness of the structural material (e.g., pipe).

Figure 5:
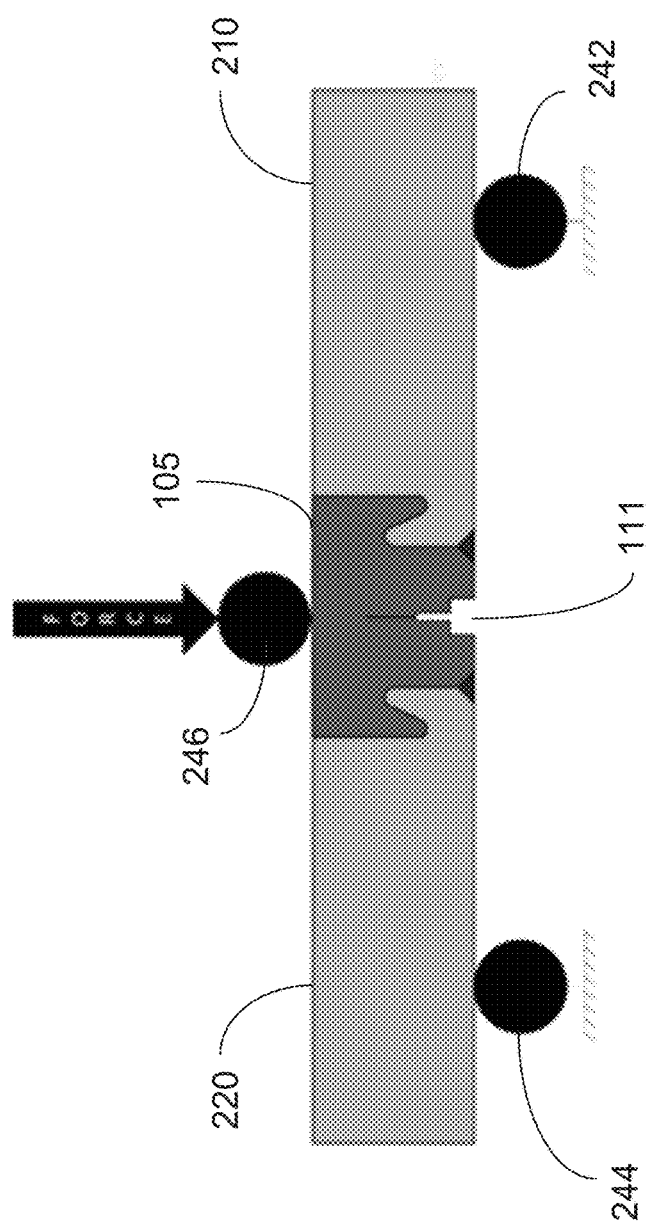
FIG. 5 is a schematic front plan view of an embodiment of an assembled test specimen according to the present invention subjected to a standard 3-point bending test.

FIG. 5 is a schematic illustration of a standard 3-point bending fracture toughness test being applied to an assembled test specimen according to an embodiment of the present invention. As shown, the assembled test specimen is positioned horizontally, with the top edge facing down. In this position, the top edge of the first lateral extension 210 is in contact with and supported by a fixed ball element 242 (shown on the right in FIG. 5), and the top edge of the second lateral extension 220 is in contact with and supported by a fixed ball element 244. A third ball element 246 is placed on the reverse side of the test specimen on the upwardly-facing rear face of notched component 105. During the test, a downward force is applied to the third ball element 246 which applies pressure to the rear face of the notched component. This force creates a bending moment that tends to open the crack formed by the central notch 111 of the notched component.

In addition to enabling measurement of in-plane fracture toughness (i.e., S-T and S-L directions), the test specimen according to the present invention provides additional advantages. Since, for a given structural material of interest (e.g., "mother plate"), only the relatively small notched components are machined from the material, while the lateral extensions can be machined from other structures having comparable mechanical properties (e.g., elastic modules and strength) as the original material of interest. For example, if the structure of interest is carbon steel, then the extensions should also be made of steel (e.g., HSLA, carbon steel, mild steel), and should not be made of a metal with distinctly different properties such as aluminum. In this manner, raw material can be economized. For example, the maximum number of samples that can be machined from a unit area of mother plate is about (1/W*B) for the S-L configuration, compared to (1/4.5W*W) for the T-L configuration and (1/4.5*W*B) for the L-S configuration, where B is a constant stipulated by the standard test requirements. Given that some standards require that B=0.5W, up to 9 more specimens per unit area can be produced by economizing on raw material in this manner.

In addition, the test specimens according to the present invention are particularly suited for environmental FT testing. Since the notched component is machined separately, there is more flexibility for carrying out FT tests in harsh environments. For example, when carrying out FT tests in a hydrogen-rich environment, one can select a material for the lateral extensions that has less sensitivity to hydrogen absorption (e.g., austenitic stainless steel) in order to concentrate the hydrogen embrittlement into the machined sample only. Additionally, the machined notched component can be exposed to the harsh environment of interest prior to coupling the sample to the lateral extensions and FT testing.

Finite Element Optimization of the Geometry of the Notched Component

Figure 6:
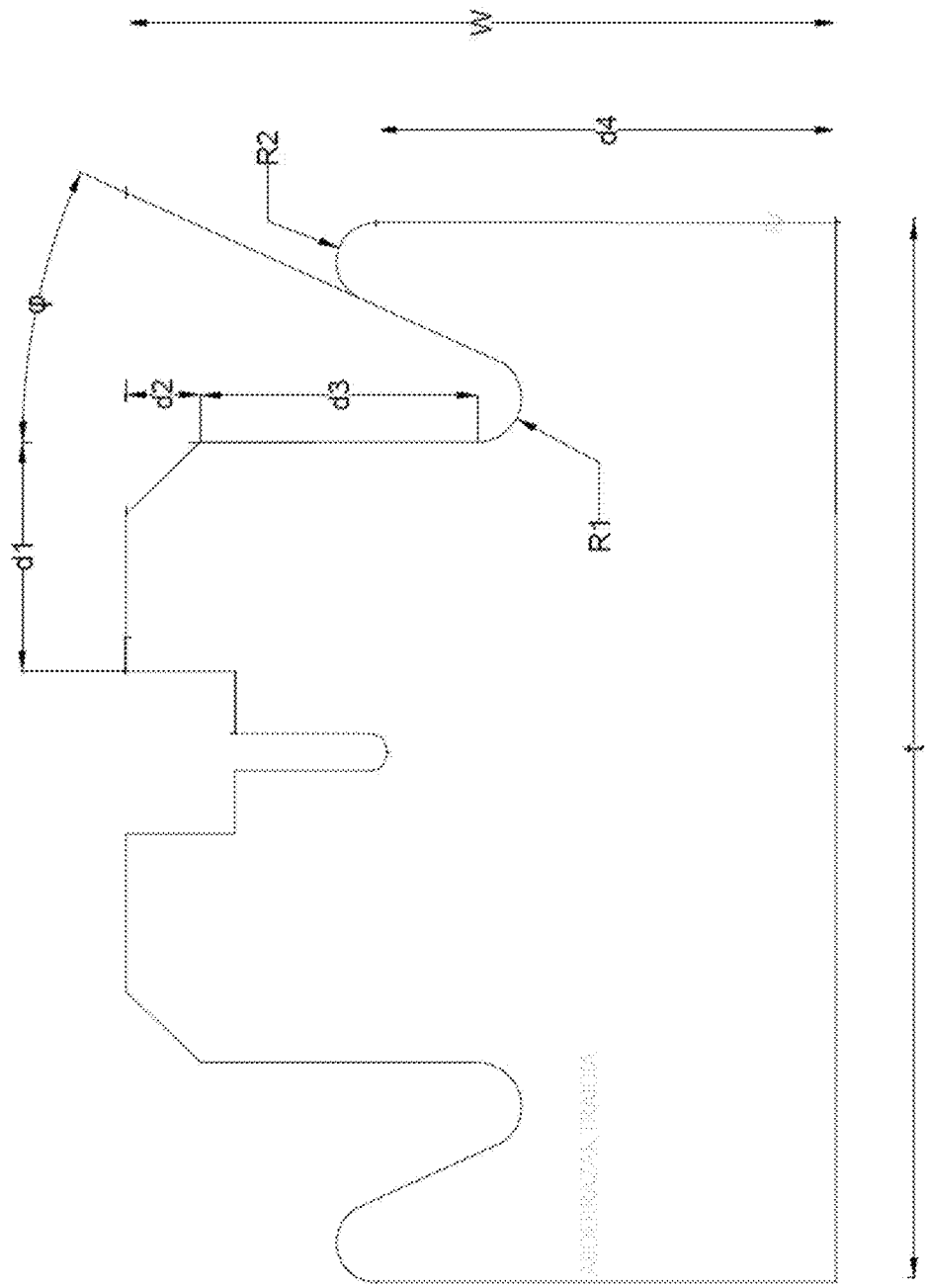
FIG. 6 is an enlarged front plan view of an embodiment of a notched component according to the present invention.

Since the notched component according to the certain embodiments present invention has a complex "W" shape, it important to select the dimensional parameters of the shape to ensure that the test specimen, when fully assembled with lateral extensions, behaves mechanically like a single-part, integral test specimen. FIG. 6 shows an enlarged plan view of an embodiment of a notched component according to the present invention. FIG. 6 illustrates several geometric parameters associated with the notched component, including certain dimensions, d1, d2, d3, d4, R1, R2, t, W and an angle φ. The notched component depicted can thus be characterized by a total of nine geometric parameters, of which the thickness (t) is based on the thickness of the structural material of interest, and W is arbitrarily fixed by the tester. The seven remaining parameters (d1, d2, d3, d4, R1, R2 and φ, which can be reduced to six variables if R1 is set equal to R2, are variables that can be optimized using either experimental tests or simulation models.

Figure 7:
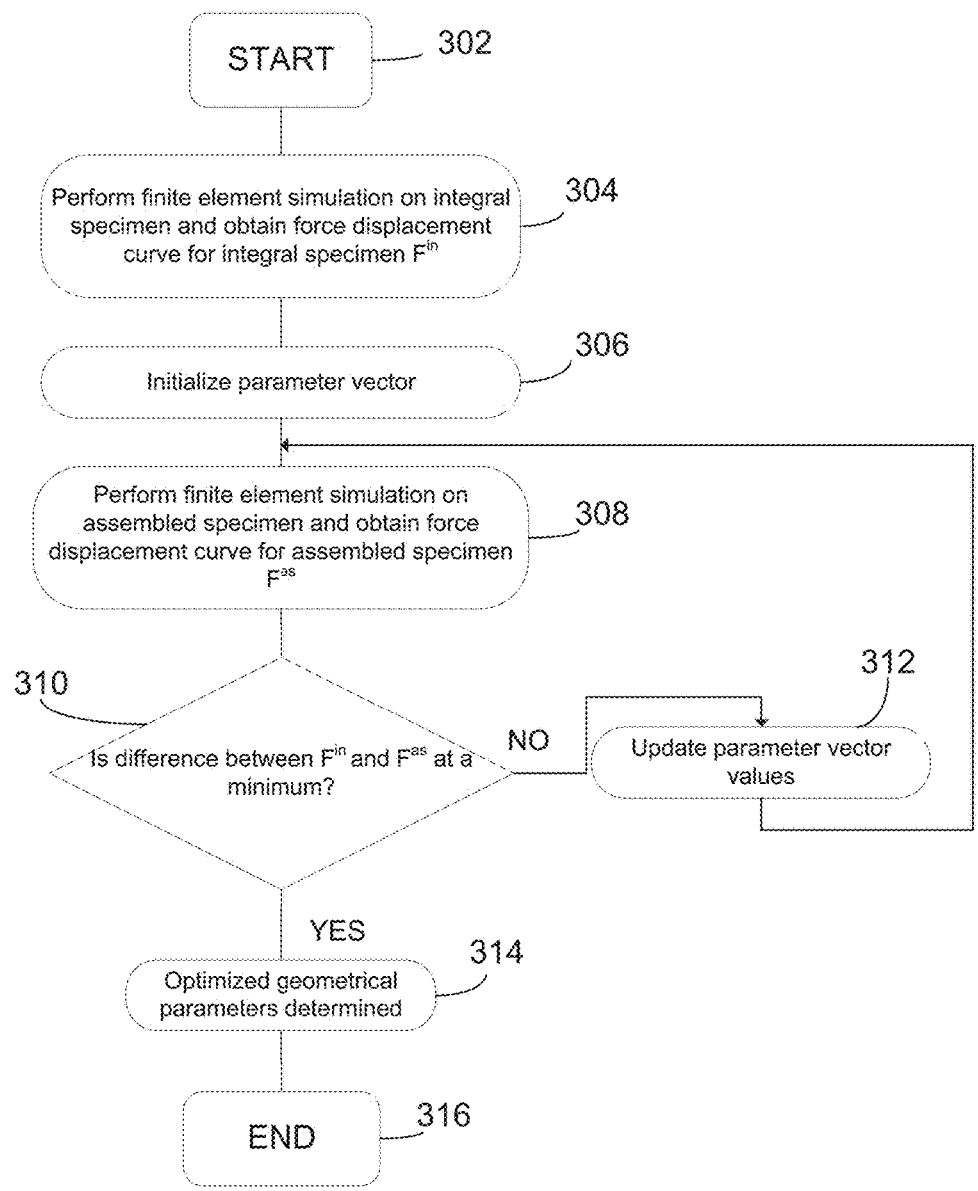
FIG. 7 is a flow chart of an exemplary method of optimizing parameter of the notched component according to the present invention.

The following discussion describes an exemplary geometric parameter optimization that may be performed for the notched component according to the present invention using program code executed on a processor of a computer system. The optimization uses a finite element analysis which simulates and compares the mechanical behavior, under a fracture toughness test, of assembled and integral test specimens having different values of the six tested parameters. The optimization seeks to find parameter values for which the assembled test specimen behaves as closely to an integral, single-part specimen as possible. FIG. 7 is a flow chart of an exemplary method for optimizing the geometric variables of the notched component according to the present invention. In step 302, the method starts. In step 304, a finite element simulation is performed on a selected design of an integral test specimen, i.e., a test specimen that is not assembled according to the present invention. The finite element simulation outputs a force displacement curve for the integral specimen, $F^{in}$. In step 306, a vector that includes the geometric parameters of the notched component of the assembled test specimen according to the present invention is initialized according to methods known in the art. In step 308, a finite element simulation is performed on an assembled test specimen according to the present invention including a notched component and lateral extensions. The output of the finite element simulation is a force displacement curve for the assembled test specimen, $F^{as}$. In step 310 it is determined whether the difference between the force displacement curves, $F^{in}$ and $F^{as}$ is at a minimum. If it is determined that the difference is not at a minimum, in step 312 the geometrical parameter vector is updated, and the method cycles back to step 308 to re-perform the finite element simulation on the updated parameters. If it is determined in step 310 that the difference between the force displacement curves, $F^{in}$ and $F^{as}$ is at a minimum, the method flows to step 314 in the finalized parameter vector of the geometrical components of the notched component are determined. The method ends in step 316. The optimization method can employ gradient descent based techniques and/or other techniques known in the art.

Simulation Example

Figure 8A:
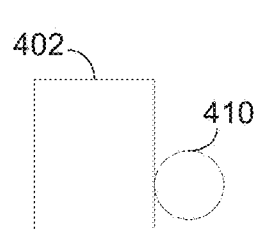
FIG. 8A is a flow chart of an optimization method for selecting values for parameters of the geometry of the machined sample according to an embodiment of the present invention.
Figure 8B:
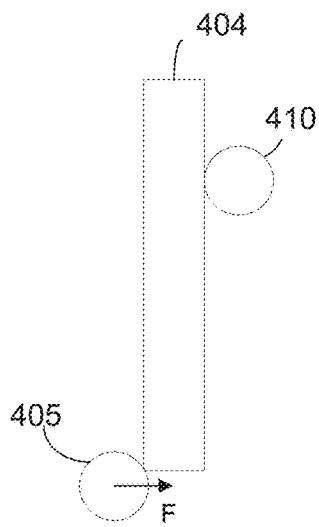
Figure 8C:
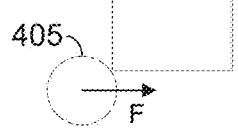
Figure 8D:
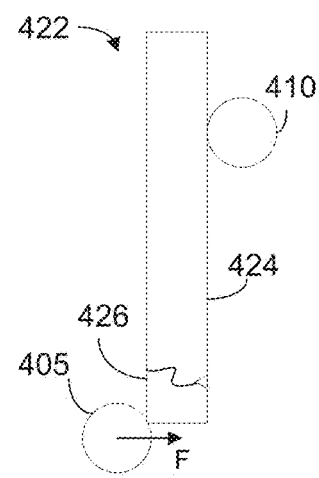

The following example describes a parameter optimization for two different planar structures, having thicknesses of 10 mm and 20 mm, common for structures in the oil & gas industry. The parameter optimization was obtained using a finite element simulation program (e.g., ANSYS® v16 "simulator") executed on a computer system. The simulation generated four separate models. Two of the models represent integral, single-part specimens, one of a 10 mm thick specimen, and the other of a 20 mm thick specimen. The two models represent assembled test specimens according to the present invention, similarly one of 10 mm thickness and the other of 20 mm thickness. As the test specimens are symmetric about their respective horizontal centers, the finite element simulations were performed on half-specimens from the center to the periphery. Schematic illustrations of the finite element models are shown in FIGS. 8A-8D. FIG. 8A shows a 20 mm thickness integral specimen 402 subjected to a compressive force by ball element 405 on the rear face at a lower left vertex, and supported toward the top of the front face by roller ball element 410. FIG. 8B shows a 10 mm thickness integral specimen 404 subjected to a compressive force by similar ball element 405 on the rear face at a lower left vertex, and supported toward the top of the front face by roller ball element 410. FIG. 8C shows a finite element model of an assembled test specimen 412 of 20 mm thickness composed of lateral extension 414 and half of the notched component 416 to which the lateral extension is coupled. Forcing ball element 405 applies compressive force onto the rear face of the notched component 416 and the front face of lateral extension 414 is supported by roller ball element 410. FIG. 8D shows a finite element model of an assembled test specimen 422 of 10 mm thickness composed of lateral extension 424 and half of the notched component 426 to which the lateral extension is coupled. Forcing ball element 405 applies compressive force onto the rear face of the notched component 426 and the front face of lateral extension 424 is supported by roller ball element 410.

In the four finite element models, the simulator used a plane strain formulation for both the integral and assembled FT test specimens. This formulation is a fair approximation in order to compare the force-displacement curves and fracture toughness parameter $K_Q$ of the two types of specimens. In addition, for all the models, a static non-linear analysis was performed using large displacement theory and employing a Newton-Raphson incremental-iterative scheme. For the integral test specimens, eight node 2D structural shell elements were used, while the roller supports were modeled as rigid objects. Contact between the specimen and roller supports was modeled using three node 2D surface to surface contact elements, with a friction coefficient equal to about 0.3.

The simulator modeled material behavior using the stress-strain curve of a High Strength Low Alloyed steel (HSLA), more particularly, FCA (Fatigue Crack Arrester) steel, which has a ferritic-bainitic structure. Boundary conditions were imposed at the rollers. Specifically, translations in either the x-direction (direction of compression) or the y-direction (along the length of the specimens) at the roller ball elements were set to zero with rotation allowed. Translations at the point of application of ball element 405 in the y-direction and rotations were also set to zero. For deriving the force-displacement curve from the simulations, a displacement ($U_x$) and was imposed at the pilot node of ball element 405 (the point at which the ball element 405 contacts the notched component). For evaluating the fracture toughness $K_Q$, a Force load ($F_x$) was imposed at the pilot node of ball element 405.

Using the boundary conditions and material behavior, the finite element simulator evaluated of the J integral parameter around the crack tip of each test specimen. The J-integral represents a way to calculate the strain energy release rate, or work (energy) per unit fracture surface area, in a material. The J-integral was evaluated through integration around closed paths around the crack using identical element edge lengths facilitating convergence of the J-integral value. The fracture toughness parameter $K_Q$ was then evaluated via J integral. The J integral can be converted to the fracture toughness parameter according to the following equation:

$$J = K_Q^2 (E(1-v^2)) \qquad 2$$

in which E is the material elastic modulus of the FCA material, J is the J integral, and K is the fracture toughness parameter.

The modeling for the assembled test specimens shown in FIGS. 8C and 8D differed somewhat in that flexible contact between the notched component and the lateral extension using was modeled using three node 2D surface-to-surface contact elements with a friction coefficient of 0.3. In addition, the coupling between the notched component and lateral extension (in the example, welding) was simulated by coupling the degrees of freedom of coincident nodes up to the maximum depth of the crack (in other words, d3 was constrained to the maximum crack depth) of 3 mm for the 20 mm specimen and 2.2 mm for the 10 mm specimen. In other respects, the modeling of the assembled specimens was identical to the modeling of the integral specimens, with the same element types, material models, boundary conditions, symmetries and loads, etc.

Figure 9A:
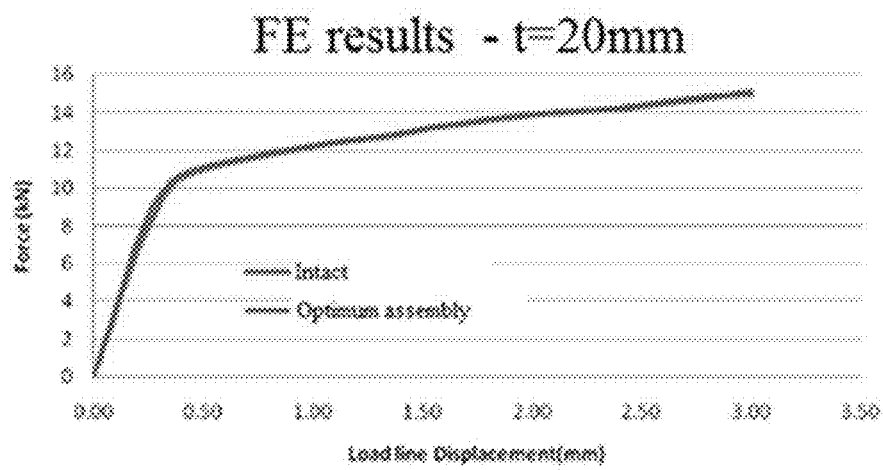
FIG. 9A and 9B are graphs of force versus load line displacement for both integral and assembled test specimens of 20 mm (FIG. 9A) and 10 mm (FIG. 9B), respectively, obtained from a finite element simulation according to the present invention.
Figure 9B:
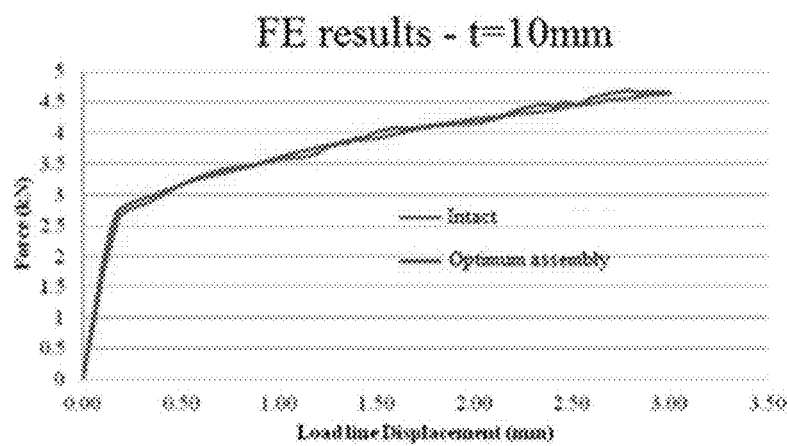

FIGS. 9A and 9B are graphs showing results of the example finite element simulation. FIG. 9A shows graphs of force versus load line displacement for both the integral and assembled test specimens of 20 mm thickness. As indicated, the graph of the assembled test specimen closely tracks the graph for the integral test specimen. FIG. 9B shows graphs of force versus load line displacement for both the integral and assembled test specimens of 10 mm thickness. The graph of the assembled test specimen also closely tracks the graph for the integral test specimen in FIG. 9B. The Force-Displacement curve results were obtained by imposing a displacement of 3 mm at the pilot node of ball element 405. The nearly identical results for the integral and assembled test specimens demonstrate that the proposed designs are mechanically acceptable for both 10 mm and 20 mm thicknesses.

Figure 10A:
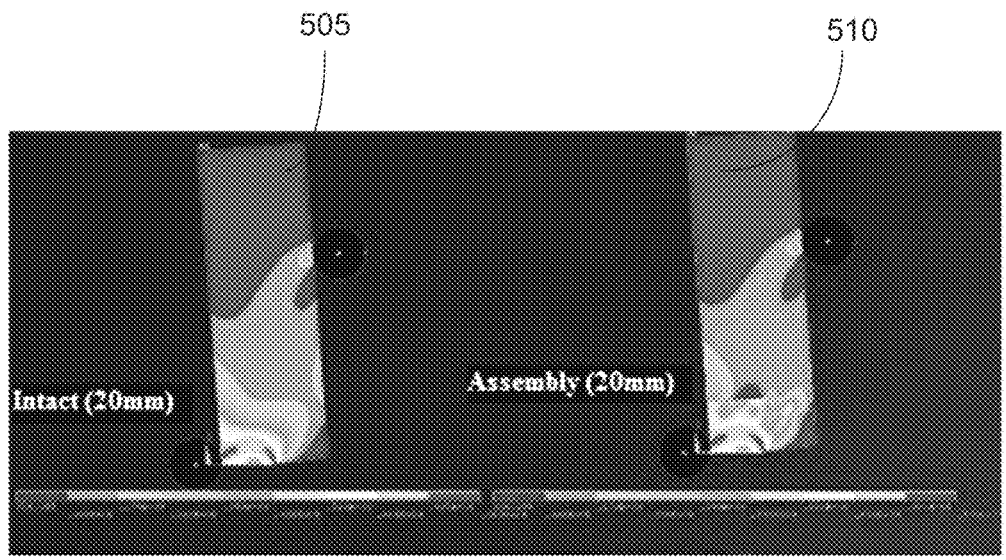
FIG. 10A and 10B are von Mises contour diagrams for both integral and assembled test specimens of 20 mm (FIG. 10A) and 10 mm (FIG. 10B), respectively, obtained from a finite element simulation according to the present invention.
Figure 10B:
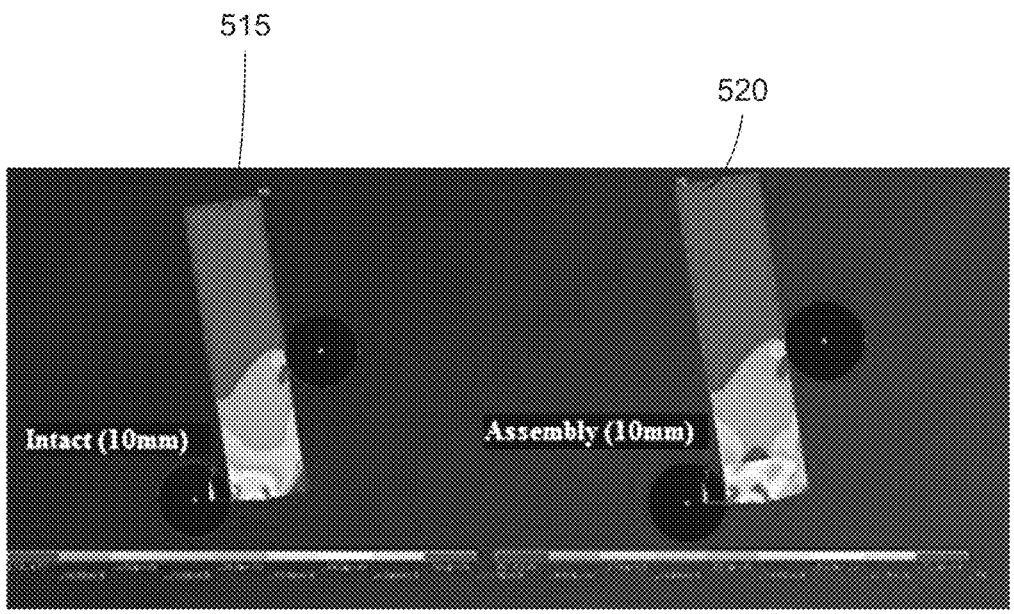

FIG. 10A shows von Mises contours obtained from the finite element models of specimens of 20 mm thickness. Von Mises contours indicate local stresses. The contour 505 on the left of FIG. 10A shows the stress field of the integral test specimen, while contour 510 on the right shows the stress field of the assembled test specimen. FIG. 10B shows similar contours obtained from the finite element models of specimens of 10 mm thickness. The contour 515 on the left of FIG. 10B shows the stress field of the integral test specimen, while contour 520 on the right shows the stress field of the assembled test specimen. Viewed together, the Von Mises contours of FIGS. 10A and 10B indicate that the local stress field around the crack zone is well captured by the assembled test specimen according to the present invention.

Table 1 shows a summary of fracture toughness parameter results of the finite element simulation of fracture toughness tests on the integral and assembled models at the two thickness. The $K_Q$ results were obtained by using an applied force $F_x$ of 2.2 kN and a notch plus crack length ($a_0$) of 4.1 mm for the 10 mm specimens and applied force $F_x$ of 6.09 kN and $a_0$ length of 10 mm for the 20 mm specimens. Table 1 provides evidence that the predicted fracture toughness indicators (J and $K_Q$) for the assembled specimens are in excellent agreement with those of the conventional single-part integral specimens.

TABLE 1

Numerical evaluation of Fracture toughness parameters

| FE Model | $K_Q$ (MPa/m$^{1/2}$) | $J_C$ N/mm | $a_0$ (mm) | $F_Q$ (kN) |
|---|---|---|---|---|
| Intact specimen (20 mm) | 46.52 | 9.56 | 10.0 | 6.09 |
| Optimum assembly (20 mm) | 47.59 | 10.01 | 10.0 | 6.09 |
| Intact specimen (10 mm) | 38.2 | 6.45 | 4.1 | 2.266 |
| Optimum assembly (10 mm) | 39.2 | 6.79 | 4.1 | 2.266 |

Experimental Tests

A. First Set of Experiments—Regular (Non-Harsh) Environment

In addition to the finite element study, several fracture toughness tests were performed on physical specimens to validate the assembled specimen designs. The fracture toughness tests were performed specifically on FCA (Fatigue Crack Arrester) steel, which was also modeled in the finite element simulations. FCA steel is a high strength ferritic-bainitic steel with following composition listed in below Table 2.

TABLE 2

Chemical Composition of FCA steel at yield stress of 420 MPa

| C | Si | Mn | Ceq* |
|---|---|---|---|
| 0.06 | 0.44 | 1.55 | 0.37 |

*Ceq = C + Mn/6 + Si/24 + Ni/40 + Cr/5 + Mo/4 + V/14 (%)

Figure 11:
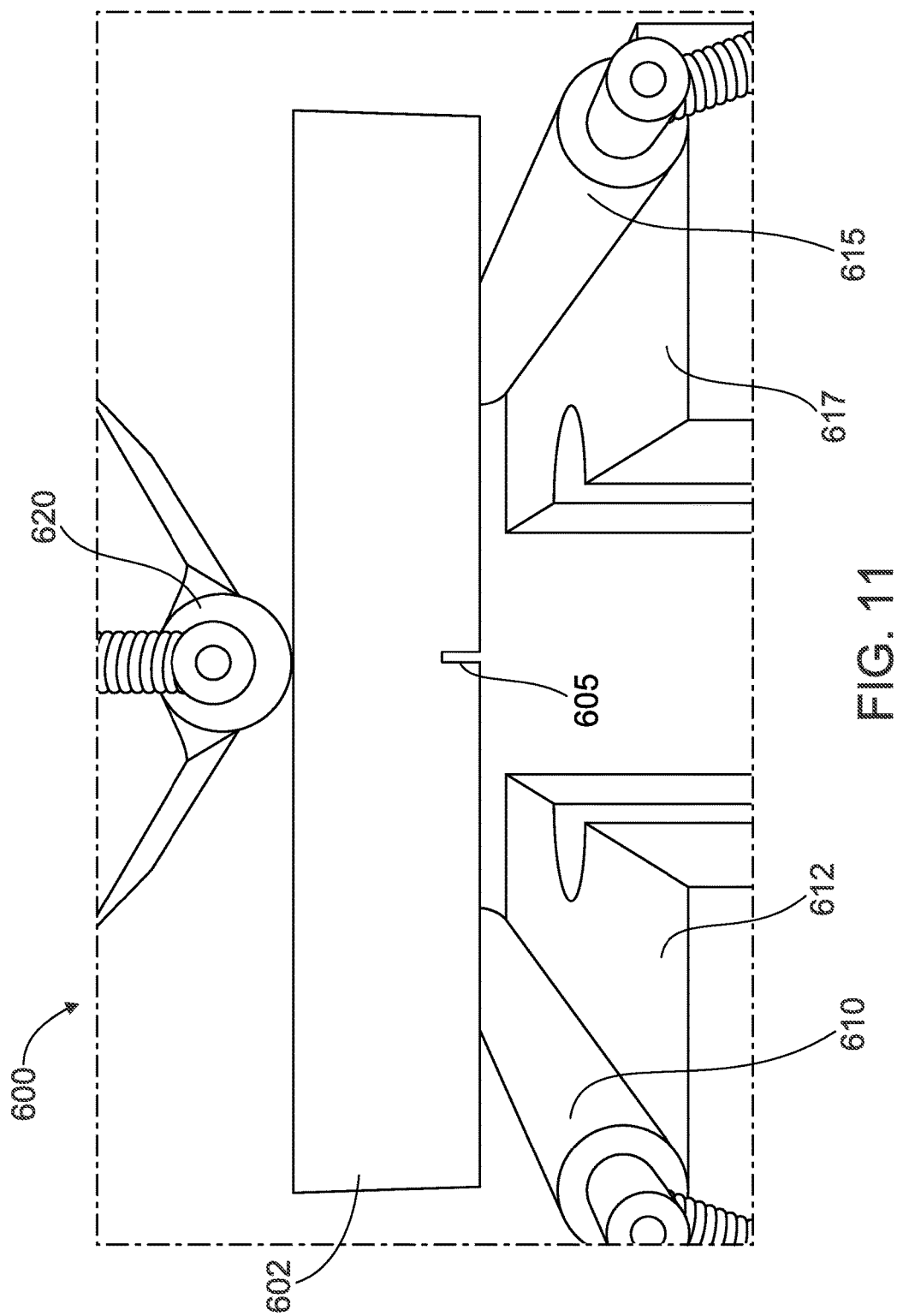
FIG. 11 is a photograph of an exemplary fracture toughness test apparatus used in testing integral and assembled test specimens according to the present invention.

As with the finite element simulation, tests were conducted on both integral and assembled test specimens at 10 mm and 20 mm thicknesses, totalling four tests. In addition, each of the 4 tests was repeated 3 times (12 tests in total) to assess the standard deviation of FT measurements. Prior to fracture toughness testing, the machined samples were notched, and fatigue pre-cracked, following the guidelines of testing standard ASTM E1820. The length of the fatigue pre-crack was measured using a MATELECT CM 7 ACPD (AC potential drop). All tests were performed on a 100 kN MTS hydraulic testing machine. A photograph showing the test apparatus 600 used for the tests is shown in FIG. 11. An integral specimen 602 having a notch 605 is shown placed horizontally on the apparatus 600 with the notch (front face of the specimen) facing downward. The specimen rests on two ball elements 610, 615, positioned respectively to the left side and right side and below the specimen. Ball element 610 rests on support block 612 and ball element 617 rests on support block 617. At the top of the apparatus a ball element positioned in contact with the center of the upwardly facing surface of the specimen exerts a downward force, tending to cause the notch 605 on the bottom of the specimen to widen. The tests measured the maximum stress intensity factor at the end of the elastic slope of the Force-Displacement curve and the maximum J integral otherwise known as $J_0$, which corresponds to the point of maximum force on the Force-displacement curve. All calculations of fracture toughness parameters were accomplished following the ASTM E1820 standard.

Table 3 lists measured FT values for integral and assembled test specimens of 20 mm thickness. Table 4 lists corresponding measured FT values for integral and assembled test specimens of 10 mm thickness. Tables 3 and 4 show close agreement between FT values of the integral and assembled test specimens.

TABLE 3

Fracture toughness results for thick specimens (20 mm)

| Specimens | $K_Q$ (MPa/ $m^{1/2}$) | $J_0$ kJ/$m^2$ | $a_0$ (mm) | $F_Q$ (kN) | $F_{max}$ (kN) |
|---|---|---|---|---|---|
| Intact specimen (20 mm) | | | | | |
| Test 1 | 46.56 | 762.65 | 9.80 | 6.38 | 11.50 |
| Test 2 | 45.86 | 791.87 | 10.00 | 6.09 | 10.77 |
| Test 3 | 48.52 | 731.58 | 10.05 | 6.36 | 10.42 |
| Average | 46.98 | 762.04 | | | |
| Standard Deviation | 1.38 | 30.15 | | | |
| Assembled specimen (20 mm) | | | | | |
| Test 1 | 45.04 | 821.58 | 9.10 | 6.70 | 13.10 |
| Test 2 | 45.84 | 795.86 | 9.35 | 6.50 | 11.36 |
| Test 3 | 44.68 | 836.86 | 8.35 | 7.34 | 13.69 |
| Average | 45.19 | 818.10 | | | |
| Standard Deviation | 0.59 | 20.72 | | | |

TABLE 4

Fracture toughness results for thin specimen (10 mm)

| Specimens | $K_Q$ (MPa/ $m^{1/2}$) | $J_0$ kJ/$m^2$ | $a_0$ (mm) | $F_Q$ (kN) | $F_{max}$ (kN) |
|---|---|---|---|---|---|
| Intact specimen (10 mm) | | | | | |
| Test 1 | 36.96 | 526.58 | 4.10 | 2.27 | 3.70 |
| Test 2 | 38.50 | 602.18 | 4.08 | 2.38 | 4.00 |
| Test 3 | 36.89 | 578.13 | 4.20 | 2.20 | 3.74 |
| Average | 37.45 | 568.96 | | | |
| Standard Deviation | 0.91 | 38.63 | | | |
| Assembled specimen (10 mm) | | | | | |
| Test 1 | 36.93 | 571.60 | 4.22 | 2.19 | 3.75 |
| Test 2 | 37.80 | 553.36 | 4.35 | 2.16 | 3.55 |
| Test 3 | 37.86 | 533.19 | 4.26 | 2.22 | 3.71 |
| Average | 37.53 | 552.72 | | | |
| Standard Deviation | 0.52 | 19.21 | | | |

With respect to the thin 10 mm specimens, the data of Tables 3 and 4 indicates that the difference between the average $K_Q$ values of the integral and the assembled specimens is ($\Delta K_Q$) is 0.08 (table 4), which is substantially less than the standard deviation of the integral specimens (0.91). The same is true of the value of $J_0$ integral for which the difference ($\Delta J_0$) is 16.24 and the standard of the integral specimens is 38.63. These experimental results demonstrate that the geometric design implemented for the notched component and assembled test specimen as a whole, according to the present invention, is well suited to evaluate the fracture toughness properties of relatively thin steel plates.

B. Second Set of Experiments—Simulation of Harsh ($H_2S$) Environment

A second set of experiments was performed to determine the effect of hydrogen on the fracture toughness properties of API X65 pipeline steel under simulated $H_2S$ conditions prevalent in pipelines while in service. Specifically, fracture toughness properties KIH and CTOD¬0 in air and at three levels of hydrogen were studies for the S-L and T-L crack directions. The fracture toughness experiments were performed on 300 mm thick X65 low carbon steel extracted from a field pipeline. A standard HIC qualification test was first performed and the results showed that the pipeline steel used in this study is HIC resistant.

The first procedure in the second set of experiments was simulating the in-service, harsh environment conditions by charging the specimen with hydrogen. Three different hydrogen concentrations ($C_H$) were established by electrolytic hydrogen charging in a 30 gm NaCl and 3 gm $NH_4SCN$ aqueous solution in which the X65 steel specimen served as the cathode with a platinum anode. The $NH_4SCN$ was used as a hydrogen recombination poison and during hydrogen charging the solution was de-aerated with $N_2$. Hydrogen pre-charging was performed for a duration of for 48 hours which has been shown to be sufficient to achieve a stable hydrogen concentration in the metal lattice of a pipeline steel.

This initial set of charging tests determines the current densities which can produce the desired $C_H$ in the X65 samples. The hydrogen content was measured in notched X65 specimens of 20 mm length, 20 mm width and 10 mm thickness, with a notch depth of 5 mm. The X65 steel samples were polished using a 600-grade emery paper, cleaned with distilled water and acetone and dried. This ex-situ hydrogen charging protocol is representative of actual conditions relevant to crack initiation and propagation in oil and gas pipelines in the field. The charging protocol allows slow hydrogen uptake and diffusion inside notched X65, simulating the uptake in the bulk of the X65 steel material and the slow hydrogen accumulation rate that occurs in the oil field.

After the X65 steel specimen was hydrogen-charged for 48 hours, it was immersed in liquid nitrogen (77K) in order to avoid fast hydrogen desorption and then transferred to a thermal desorption spectroscopy (TDS) measuring cell and inserted into a furnace. Argon flow (around 60 ml/min) was supplied and monitoring of the spectrometer signal was initiated. The duration o from immersion in the nitrogen bath to the signal monitoring was about 10 minutes. operation (from liquid N2 bath to MS monitoring of signals) lasted around 10 min. Sample signals were recorded for 6 minutes at room temperature, i.e. the sample was kept at room temperature for 6 minutes, in order to allow for flow/pressure equilibration, followed by a temperature ramp (3° C./min) up to 700 ° C. was initiated. After reaching 700° C. the sample was maintained at this temperature for around 3 hours. At the end of the 3-hour period, the furnace was turned off and natural cooling commenced. The results of the TDS measurements are used to establish the current densities required to achieve the target bulk. hydrogen concentrations After charging the X65 specimen, in-service conditions were simulated by establishing a steady state $C_H$ in the bulk of the X65 steel. The following empirical formula was used to evaluate the steady-state $C_H$ in the bulk of the steel after the conclusion of the hydrogen charging based on pH and $H_2S$ partial pressure:

$$CH_{measured} = 3.1 + 0.56 \log(pH2S) - 0.17 pH \quad (2)$$

In which the units of $CH_{measured}$ are ppmw and $pH_2S$ the partial pressure of $H_2S$ expressed in MPa.

Three levels of $H_2S$ partial pressure and pH were selected in order to cover the three different regions of environment severity specified in ISO 15156-2.

The hydrogen concentrations for the three levels of environmental severity selected in this study are shown in Table 5. Proposed hydrogen concentration values, after evaluation for the three levels of pH and $H_2S$ partial pressure are $C_H$-1 at 0.5 ppmw, $C_H$-2 at ppmw, and $C_H$-3 at 2 ppmw.

TABLE 5

Hydrogen Concentrations for $H_2S$ environments

| Level | CH (ppmw) | CH corrected (ppmw) | pH | pH2S (MPa) |
|---|---|---|---|---|
| 1 | 0.4 | 0.44 | 6 | 0.001 |
| 2 | 0.87 | 0.96 | 5.5 | 0.005 |
| 3 | 1.86 | 2.05 | 4 | 0.1 |

Figure 12A:
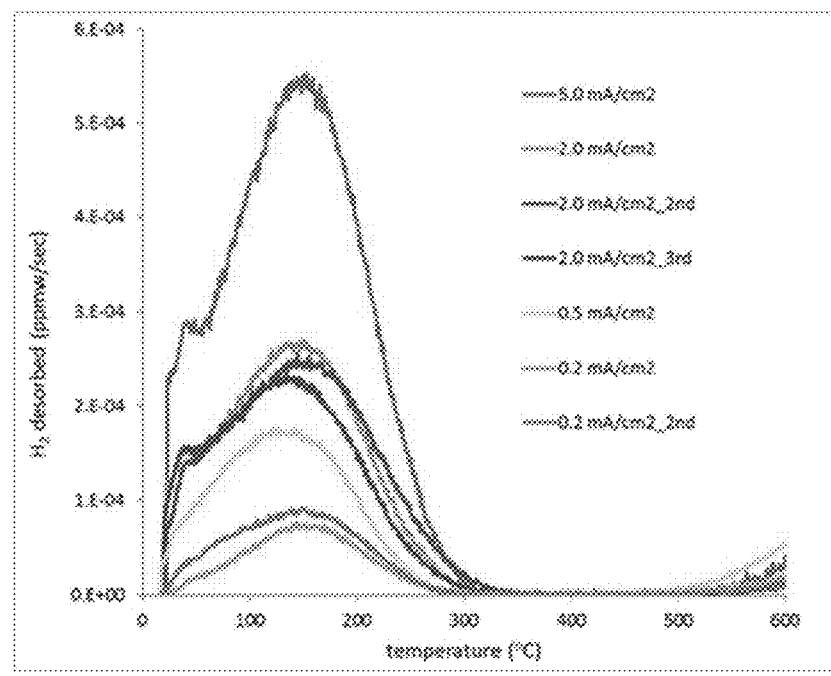
FIGS. 12A and 12B are thermal desorption spectroscopy (TDS) spectrographs showing hydrogen desorption from a single-notch bend (SEB) test specimen as a function of temperature at different current densities (FIG. 12A) and as a function of both time and temperature at different current densities (FIG. 12B).
Figure 12B:
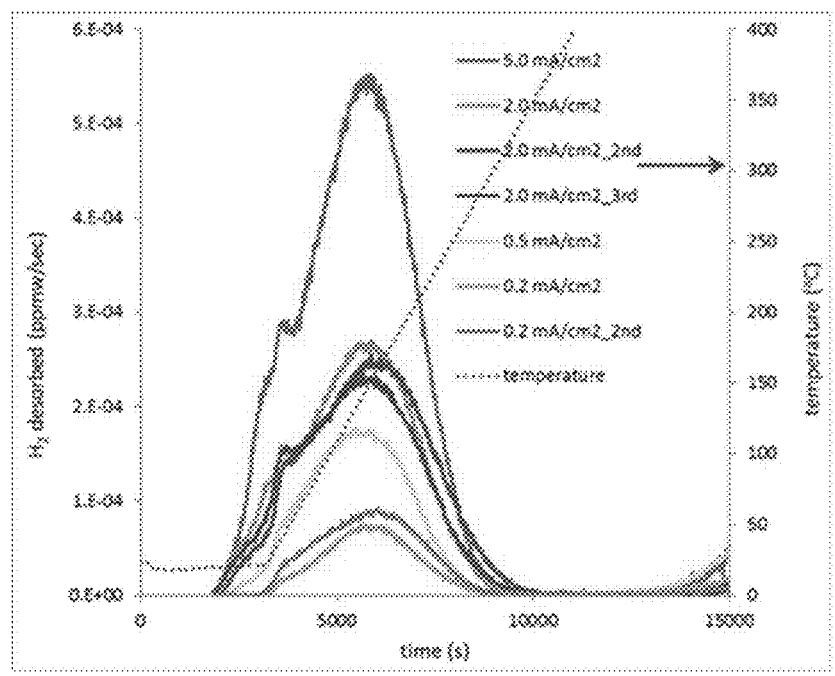

The current densities (established by TDS) that correspond to the three target CH levels were used to pre-charge fracture toughness SEB (Single Edge-notch Bending) specimens for 48 hours, prior to ex-situ fracture toughness testing. TDS experiments were performed to determine the current densities. In the experiments, the current density was varied from 0.2 mA/cm2 to 5 mA/cm2. FIG. 12A is a TDS spectrograph showing hydrogen desorption from a single-notch bend (SEB) test specimen as a function of temperature at different current densities, and FIG. 12B is a TDS spectrograph showing hydrogen desorption at different current densities as a function of both time and temperature. From the TDS measurements, the following selections were made: 5 mA/cm² for pre-charging the fracture toughness specimens with $C_H$ of 2 ppmw; 2 mA/cm² for $C_H$ of 1 ppmw; and 0.5 mA/cm² for $C_H$ for 0.5 pppmw.

In the fracture toughness tests of X65 specimens for the T-L direction, the parameter $K_Q$ was used as the maximum stress intensity factor for fracture toughness testing in air, and $K_{IH}$ for the maximum value of the stress intensity factor of hydrogen pre-charged specimens. Furthermore, the K values specified the hydrogen concentrations, for example, $K_{IH0.5}$ for the case of hydrogen charged specimens with 0.5 ppmw hydrogen concentration, $K_{IH1}$ for hydrogen charged specimens with 1 ppmw hydrogen concentration and finally $K_{IH2}$ for hydrogen charged specimens with 2 ppmw. Similarly, the maximum CTOD (crack tip opening displacement) parameter was distinguished in this manner. The X65 specimens tested in air yielded an average of $K_Q$=50.38 MPa m1/2 and $CTOD_0$=0.78 mm; the X65 specimens with 0.5 ppmw hydrogen concentration, yielded an average of $K_{IH0.5}$=50.78 MPa m1/2 and $CTOD_{OH0.5}$=0.52 mm; the X65 specimens with 1 ppmw CH, yielded an average of $K_{IH1}$=50.99 MPa m1/2 and $CTOD_{OH1}$=0.17 mm; and the X65 specimens with 2 ppmw CH, show an average of $K_{IH2}$=50.36 MPa m1/2 and $CTOD_{OH2}$=0.14 mm. Similarly, with respect to cracks oriented in the S-L direction, the X65 specimens tested in air yielded an average of $K_Q$=52.43 MPa m1/2 and $CTOD_0$=0.98 mm; the X65 specimens with 0.5 ppmw CH yielded an average of $K_{IH0.5}$=47.25 MPa m1/2 and $CTOD_{OH0.5}$=0.90 mm; the X65 specimens with 1 ppmw CH, yielded an average of $K_{IH1}$=46.81 MPa m1/2 and $CTOD_{OH1}$=0.32 m; and the X65 specimens with 2 ppmw hydrogen concentration yielded an average of $K_{IH2}$=45.96 MPa m1/2 and $CTOD_{OH2}$=0.39 mm.

Figure 13A:
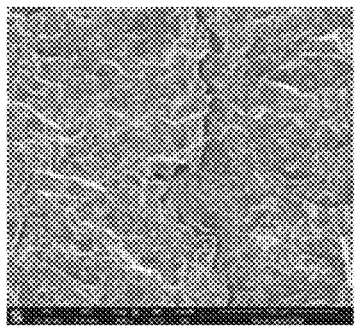
FIG. 13A to 13H are scanning electron microscope (SEM) micrographs of cracks of fractured test specimens tested in both air and hydrogen environments in the S-L and T-L direction.
Figure 13B:
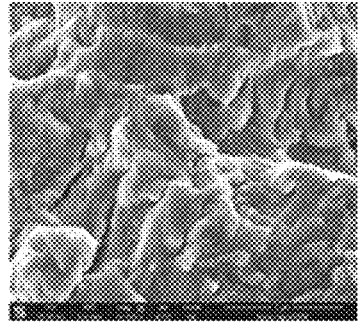
Figure 13C:
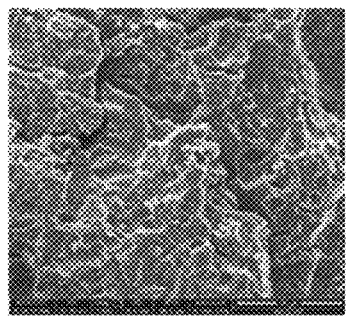
Figure 13D:
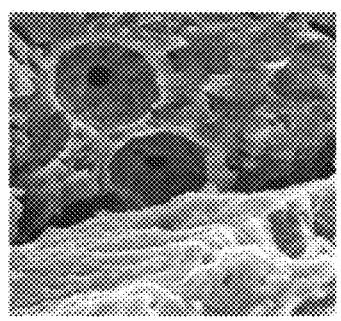
Figure 13E:
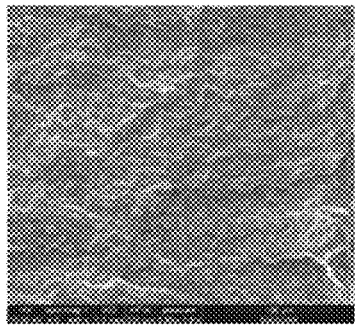
Figure 13F:
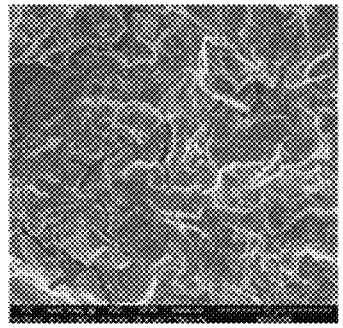
Figure 13G:
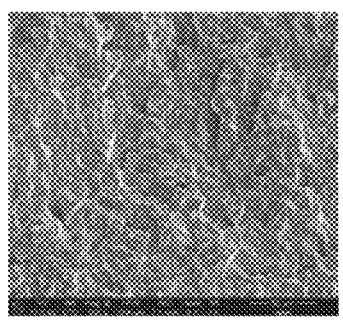
Figure 13H:
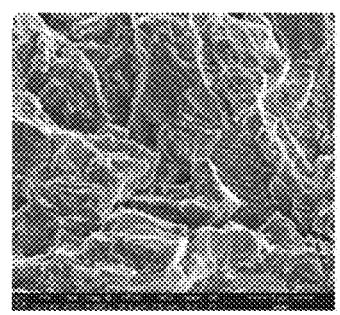

To better understand the failure mechanism underlying hydrogen induced fracturing, fractured surfaces of X65 steel in the S-L and T-L directions were analyzed using a scanning electron microscope (SEM). Specimens tested in air and at extreme hydrogen environment (2 PPM) were selected for SEM analysis. FIGS. 13A and 13B are low and high-magnification micrographs, respectively, of the fracture surface of an X65 specimen fractured in the S-L direction in air. As shown, at low relative magnification of FIG. 13A, the fracture surface appears smooth with visible secondary cracks while at the high higher magnification of FIG. 13B, the micrograph shows presence of very fine striations (beach marks) all over the crack surface. The beach marks are signatures of ductile failure. FIGS. 13C and 13D are low and high-magnification micrographs, respectively, of the fracture surface of an X65 specimen fractured in the S-L direction in a hydrogen environment (2 ppm). In contrast to the micrograph of FIG. 13A, the micrograph of FIG. 13C exhibits rough surface features with large continuous secondary cracks. At high magnification shown in FIG. 13D, pitting can be observed due to the presence of hydrogen charging. FIGS. 13E and 13F are low and high-magnification micrographs, respectively, of the fracture surface of an X65 specimen fractured in the T-L direction in air. The micrographs of FIGS. 13E and 13F demonstrate that the fracture surface of X65 tested in the T-L direction in air is largely similar to the fracture surface obtained in the S-L direction obtained in air, with the exception of the presence of more striations. The blue arrows in FIG. 13F pointing out beach marks and the red arrows highlight secondary cracks. FIGS. 13E and 13F are low and high-magnification micrographs, respectively, of the fracture surface of an X65 specimen fractured in the T-L direction in a hydrogen environment (2 ppm). In the contrast to the fracture surface observed in the S-L, the fracture surface of X65 tested in T-L direction in a hydrogen environment (2 PPM) exhibits smoother surface features with few secondary cracks and no clear evidence of corrosion (pits). However, striations are visible and comparable to ones observed in X65 sample tested T-L direction in air.

Figure 14A:
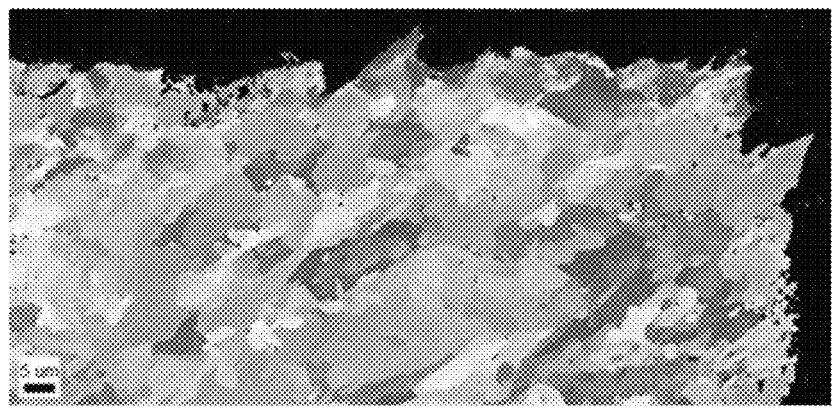
FIG. 14A and 14B show electron backscatter diffraction (EBSD) inverse pole maps from an X65 parallel (S-L) sample tested in air (FIG. 14A) and in a hydrogen environment (FIG. 14B).
Figure 14B:
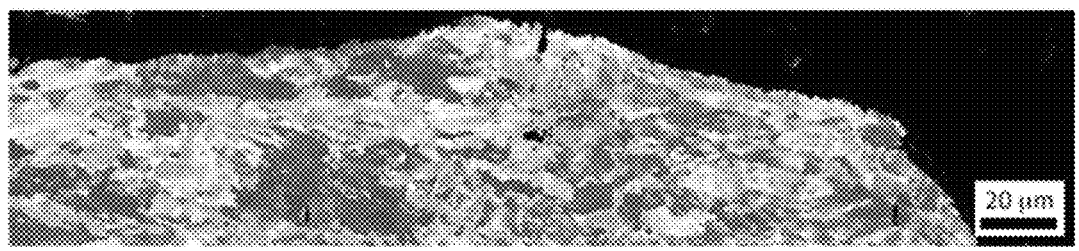

To further investigate the mechanisms by which specimens fracture in air and under hydrogen environment, electron backscatter diffraction (EBSD) mapping was conducted at the edge of the notched region and the crack propagation path. All tested samples whether in air or hydrogen-charged showed similar crack propagation features, confirming that the main crack of a fracture propagates through the grains with random orientation and in the presence of fine grain structures. FIG. 14A shows an EBSD inverse pole map from an X65 parallel (S-L) sample tested in air which shows distribution of grains and their orientation. FIG. 14A indicates the zig-zag configuration of the crack tip edge crossing all the grains. FIG. 14B shows an EBSD inverse pole map from an X65 parallel (S-L) sample tested in a hydrogen environment (2 ppm). The map of FIG.

14B also shows the zig-zag configuration of the crack tip edge crossing all the grains. The EBSD maps of FIGS. 14A and 14B show that there is no difference in the propagation mode of the crack at the vicinity of the crack path between the two different environments. All grains are crossed regardless their orientations, their shape or their size.

To shed light on the hardness properties of the X65 test specimens near and distal from the notched regions of the specimens, micro indentation tests were performed on the specimens prior to fracture toughness tests. The results obtained indicate that the Vickers hardness of the matrix region (distal from the notch) is about 236 and in the notch region the Vickers hardness is about 193. These values are in the same order of magnitude relative to the standard deviation and therefore it can be concluded that there is no noticeable change in the Vickers hardness in the tested specimens whether in air or after charged with hydrogen.

Figure 15A:
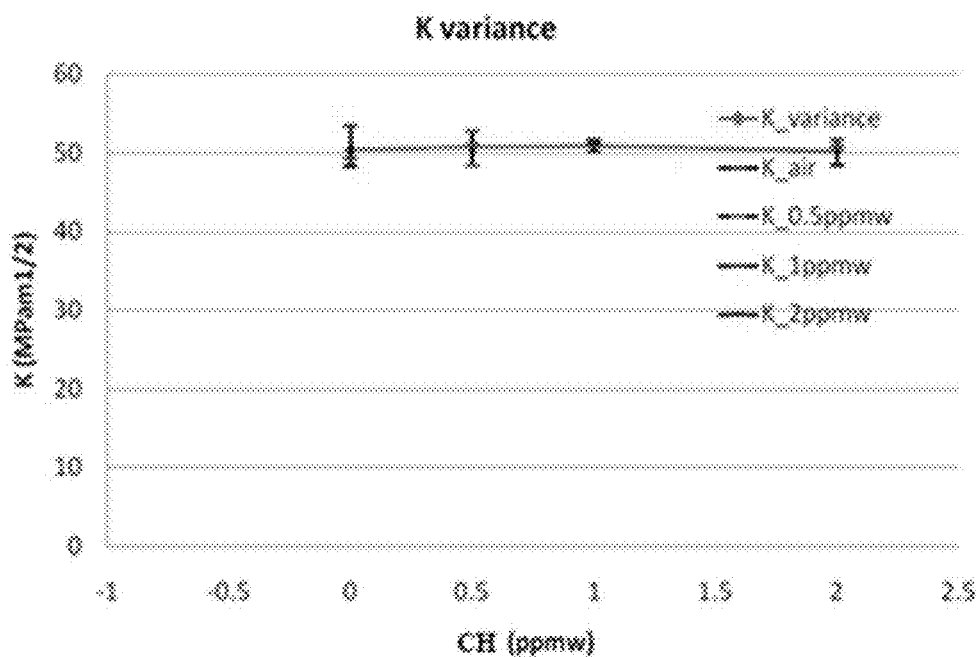
FIGS. 15A is a graph of maximum stress intensity factor (K) versus bulk hydrogen concentration for an X65 test specimen.
Figure 15B:
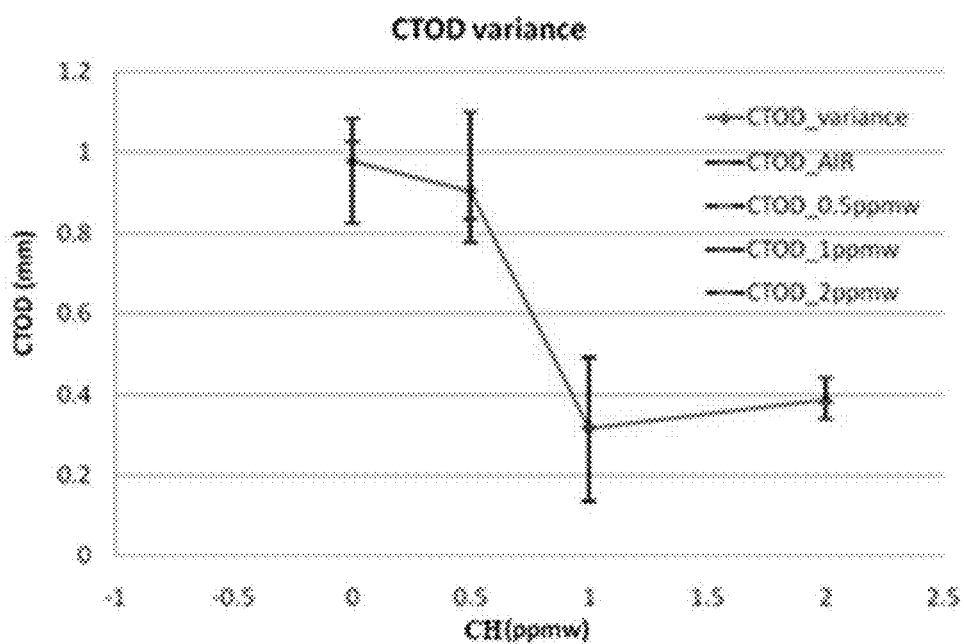
FIG. 15B is a graph of crack tip opening displacement versus bulk hydrogen concentration for an X65 test specimen fractured in the T-L direction.
Figure 16A:
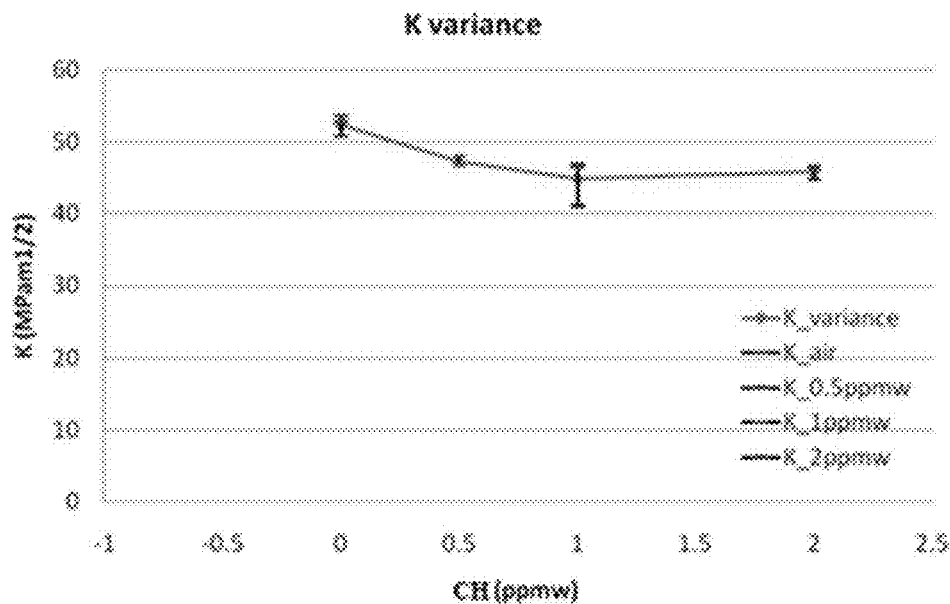
FIGS. 16A and 16B is a graph of crack tip opening displacement versus bulk hydrogen concentration for an X65 test specimen fractured in the S-L direction
Figure 16B:
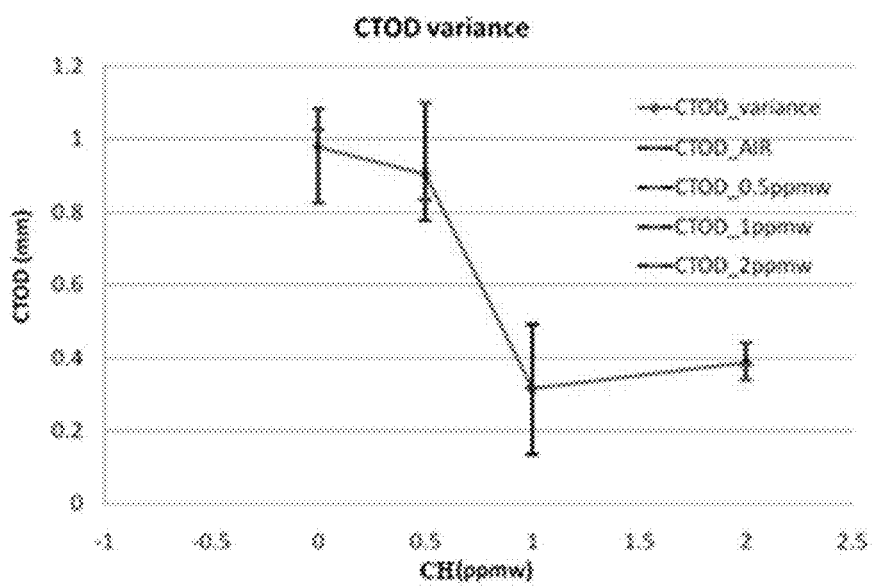

FIG. 15A is a graph of maximum stress intensity factor K versus bulk hydrogen concentration (CH). In FIG. 15A it is observed that CH up to 2 ppmw has no effect on K for a crack plane in the T-L direction. FIG. 15B shows a corresponding graph of crack tip opening displacement (CTOD) versus CH. FIG. 15B shows that hydrogen concentration plays a significant role in the reduction of the maximum CTOD value. For example, there is a 33.4% reduction in CTOD as the hydrogen concentration increases from 0.0 ($CTOD_0$) to 0.5 ppm ($CTOD_{OH0.5}$), the CTOD drops by a 77.7% reduction at $CTOD_{OH1}$ (1 ppm) and finally an 82.3% reduction at $CTOD_{OH2}$ (2 ppm) (all compared to $CTOD_0$). FIGS. 16A and 16B are analogous graphs of K and CTOD versus hydrogen concentration for specimens having a crack plane in the S-L direction. FIG. 16A shows that with increasing $C_H$, K is gradually degraded, with a 9.9% reduction of $K_{IH0.5}$, a 14.4% reduction at $K_{IH1}$ and a 12.4% reduction at $K_{IH2}$ (all compared to $K_Q$). In the same manner, FIG. 16B indicates that hydrogen concentration plays a significant role in the reduction of the maximum CTOD value. The maximum CTOD is degrades with a 7.5% reduction at $CTOD_{OH0.5}$, followed by a dramatic 67.7% reduction at $CTOD_{OH1}$, and a 60.45% reduction at $CTOD_{OH2}$ (all compared to $CTOD_0$).

The overall results demonstrate a reduction of maximum CTOD in both T-L and S-L directions by increasing $C_H$ in the bulk of the X65 steel, which is more pronounced for the T-L direction. On the other hand, it is observed that maximum K is not affected in the T-L direction by increasing $C_H$, while in the S-L direction there is a noticeable reduction in K caused by increased $C_H$. Furthermore, when fracture toughness results are compared between the two directions, a 3.9% difference in maximum $K_Q$ and a 20% difference in maximum $CTOD_0$ between the T-L and S-L direction is shown for measurements in air. A similar trend is also evident for the hydrogen-charged specimens, where in the T-L direction there is no reduction of maximum K but in the S-L direction there is reduction up to 14.4%. The same trend can be noticed when comparing the maximum CTOD values in different directions. Although in both directions they have been reduced, they have different reduction rates for each direction. It is noteworthy to point out that in many Engineering Critical Assessment (ECA) tools, the most widely used fracture toughness parameter for assessing reaming life time or limit is the stress intensity factor (e.g., critical stress intensity factor or the maximum K). Nevertheless, it has been shown in this work that in tests, while the maximum K remains unaffected the CTOD is greatly reduced. It is of great interest to accommodate CTOD in the ECA tools in order to assess the complete effect of a hydrogen environment in the assessment tool, since CTOD encompasses maximum K. In conclusion, the experiments performed showed that crack in the S-L direction develop with unique characteristics different from other directions. Development of an assembled test specimen target for testing hydrogen-induced fracturing in this direction is therefore an important tool for assessing pipe metal condition in harsh environments.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements. For the purpose of brevity certain elements of which there are a large number have been referred to by subset including the initial use of "e.g." which in subsequent cases are referred to without the use of "e.g." It is to be understand that the subset referred to by "e.g." refers to all similar elements, and that the later use of the subset without "e.g." should not be limiting but should also be understood to represent all such similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes can be made and equivalents can be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of testing a material in a standard test for in-plane fracture toughness evaluation, the material sample of a type used in a wall of a structure, the method comprising:

obtaining a sample of the wall of the structure;

shaping the sample into a notched component, the notched component including a flat bottom surface having a thickness dimension equal to a thickness of the wall of the structure, and a profiled top surface, the profiled top surface having a central notch oriented perpendicular to a plane of the bottom surface, a first socket on a first side of the central notch, and a second socket on a second side of the central notch;

assembling a test specimen which increases an effective thickness of the sample beyond the thickness of the bottom surface of the notched component by coupling a first lateral extension to the first socket and a second lateral extension to the second socket of the notched component;

applying a standard fracture toughness test to the so-assembled test specimen in order to evaluate the fracture toughness of the material in an in-plane direction; and performing a finite element simulation of fracture toughness using a programmed computer and data from the standard fracture toughness test to determine optimal geometric parameters for the notched component.

2. A method of testing a material in a standard test for in-plane fracture toughness evaluation, the material sample of a type used in a wall of a structure, the method comprising:

obtaining a sample of the wall of the structure;

shaping the sample into a notched component, the notched component including a flat bottom surface having a thickness dimension equal to a thickness of the wall of the structure, and a profiled top surface, the profiled top surface having a central notch oriented perpendicular to a plane of the bottom surface, a first socket on a first side of the central notch, and a second socket on a second side of the central notch;

assembling a test specimen which increases an effective thickness of the sample beyond the thickness of the bottom surface of the notched component by coupling a first lateral extension to the first socket and a second lateral extension to the second socket of the notched component;

applying a standard fracture toughness test to the so-assembled test specimen in order to evaluate the fracture toughness of the material in an in-plane direction; and prior to applying the standard fracture toughness test, charging the notched component with hydrogen.

3. The method of claim 2, wherein the notched component is charged with hydrogen over a duration until the hydrogen concentration reaches a desired level.

4. The method of claim 2, further comprising determining a current density required to charge the notched component to a target steady-state hydrogen concentration.

5. The method of claim 2, further comprising determining a difference in fracture properties between S-L and T-L directions at a plurality of hydrogen concentration levels.

6. An apparatus for testing a material used in a wall of a structure for fracture toughness, the apparatus comprising:

a notched component made from a sample of the material of the structure shaped to have (a) a bottom surface having a width equal to a thickness of the wall of the structure, (b) a profiled top surface, the profiled top surface having a central notch, (c) a first socket on a first side of the central notch, and (d) a second socket feature on a second side of the central notch;

a first lateral extension coupled to the first socket of the notched component; and a second lateral extension coupled to the second socket of the notched component, wherein the first and second lateral extensions extend an effective width of the notched component to provide an assembled test specimen of sufficient length to be used in a standard fracture toughness test, and wherein the notched component is charged with hydrogen.

* * * * *